(12) United States Patent
Thomas et al.

(10) Patent No.: US 9,302,102 B2
(45) Date of Patent: Apr. 5, 2016

(54) ELECTRO-THERAPEUTIC STIMULATOR

(75) Inventors: Gary Edward Thomas, Parker, CO (US); Denis E. Thompson, Lakeville, MN (US); Franklin Williard Schroeder, Jr., Lakeville, MN (US); Donald Anthony Demma, Castle Rock, CO (US)

(73) Assignee: ARP Manufacturing LLC, Centennial, CO (US)

( * ) Notice: Subject to any disclaimer, the term of this patent is extended or adjusted under 35 U.S.C. 154(b) by 1401 days.

(21) Appl. No.: 12/898,520

(22) Filed: Oct. 5, 2010

(65) Prior Publication Data

US 2011/0082524 A1 Apr. 7, 2011

Related U.S. Application Data

(60) Provisional application No. 61/248,694, filed on Oct. 5, 2009.

(51) Int. Cl.
*A61N 1/36* (2006.01)

(52) U.S. Cl.
CPC ........ *A61N 1/36003* (2013.01); *A61N 1/36014* (2013.01); *A61N 1/36171* (2013.01); *A61N 1/36021* (2013.01); *A61N 1/36175* (2013.01)

(58) Field of Classification Search
CPC ........... A61N 1/36003; A61N 1/36171; A61N 1/36175; A61N 1/36014; A61N 1/36021
USPC ......... 607/50, 52, 59, 67–72, 76, 115, 118, 2, 607/46, 48, 116
See application file for complete search history.

(56) References Cited

U.S. PATENT DOCUMENTS

| | | |
|---|---|---|
| 2,532,788 A | 12/1950 | Sarnoff |
| 2,771,554 A | 11/1956 | Gratzl |
| 3,640,284 A | 2/1972 | De Langis |
| 3,833,005 A | 9/1974 | Wingrove |
| 3,908,669 A | 9/1975 | Mau et al. |
| 4,019,519 A | 4/1977 | Geerling |
| 4,071,033 A | 1/1978 | Nawracaj et al. |
| 4,121,594 A | 10/1978 | Miller et al. |
| 4,153,061 A | 5/1979 | Nemec |
| 4,305,402 A | 12/1981 | Katims |
| 4,315,503 A | 2/1982 | Ryaby et al. |
| 4,374,524 A | 2/1983 | Hudek et al. |
| 4,392,496 A | 7/1983 | Stanton |

(Continued)

OTHER PUBLICATIONS

ARP Manufacturing, LLC, Ride the Wave, Arpwave, powered muscle stimulator operation guide, Sep. 18, 2007.

*Primary Examiner* — Catherine Voorhees
*Assistant Examiner* — Roland Dinga
(74) *Attorney, Agent, or Firm* — Shewchuk IP Services, LLC; Jeffrey D. Shewchuk

(57) ABSTRACT

An electro-therapeutic stimulator provides an output signal having a first controllable main pulse periodic-exponential signal and a second background pulse periodic-exponential signal. The main pulse signal is controllable, preferably to a digital numerical value of 1 to 500 pulses per second, to a digital, numerical value of duty cycle, and to a digital numerical value of balance. The signal is produced using a class D amplifier and with a transformer optimized for the background pulse (such as at 10 kHz) rather than for the main pulse. The electro-therapeutic stimulator includes a counter which forces purchasing of durations of signal time for ongoing use of the stimulator, and a challenge code procedure for facilitating additional time purchases.

17 Claims, 11 Drawing Sheets

(56) References Cited

U.S. PATENT DOCUMENTS

| | | |
|---|---|---|
| 4,505,275 A | 3/1985 | Chen |
| 4,535,777 A | 8/1985 | Castel |
| 4,556,051 A | 12/1985 | Maurer |
| 4,580,570 A | 4/1986 | Sarrell et al. |
| 4,690,145 A | 9/1987 | King-Smith et al. |
| 4,719,922 A | 1/1988 | Padjen et al. |
| 4,763,656 A | 8/1988 | Nauman |
| 4,850,357 A | 7/1989 | Bach, Jr. |
| 5,107,835 A | 4/1992 | Thomas |
| 5,109,486 A * | 4/1992 | Seymour .................. 709/224 |
| 5,109,846 A | 5/1992 | Thomas |
| 5,109,848 A * | 5/1992 | Thomas et al. ............. 607/68 |
| 5,257,623 A | 11/1993 | Karasev et al. |
| 5,776,173 A | 7/1998 | Madsen, Jr. et al. |
| 5,841,866 A | 11/1998 | Bruwer et al. |
| 6,564,103 B2 | 5/2003 | Fischer et al. |
| 6,584,358 B2 | 6/2003 | Carter et al. |
| 7,117,034 B2 | 10/2006 | Kronberg |
| 7,499,746 B2 | 3/2009 | Buhlmann et al. |
| 2003/0060740 A1 * | 3/2003 | Faghri ...................... 601/15 |

\* cited by examiner

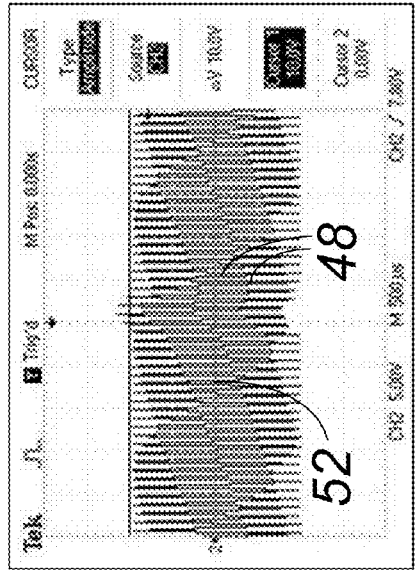
PRIOR ART FIG. 6
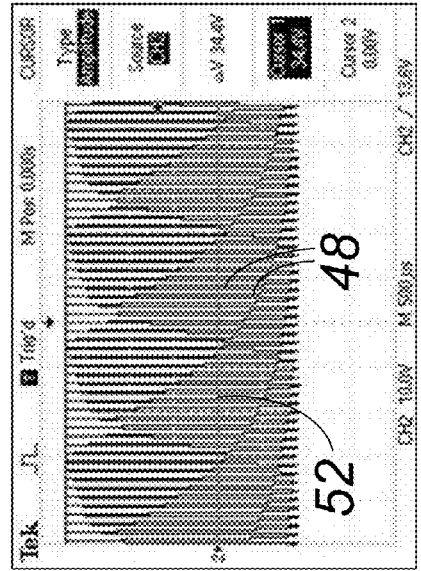
PRIOR ART FIG. 7
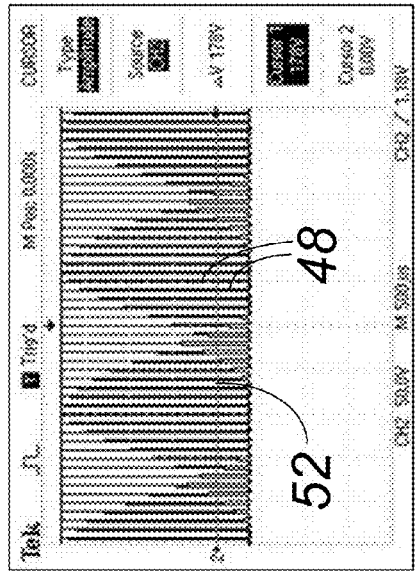
FIG. 8
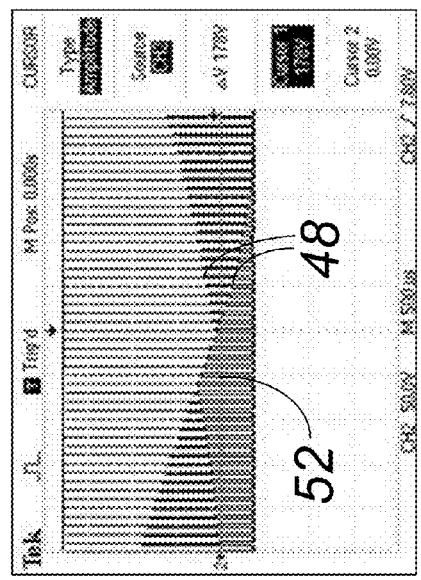
FIG. 9

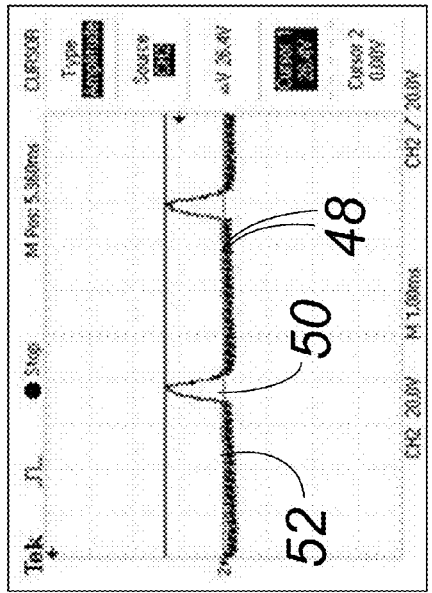
PRIOR ART FIG. 10
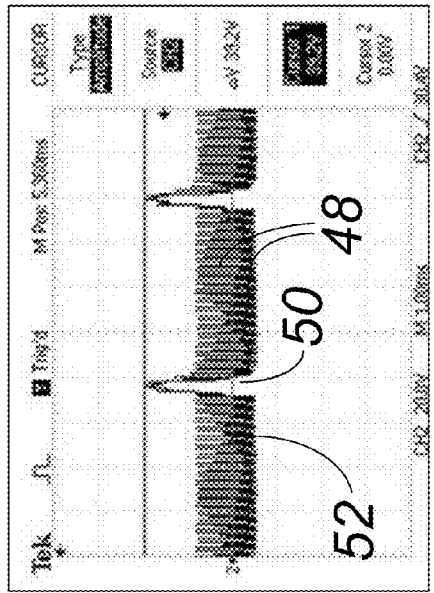
PRIOR ART FIG. 11
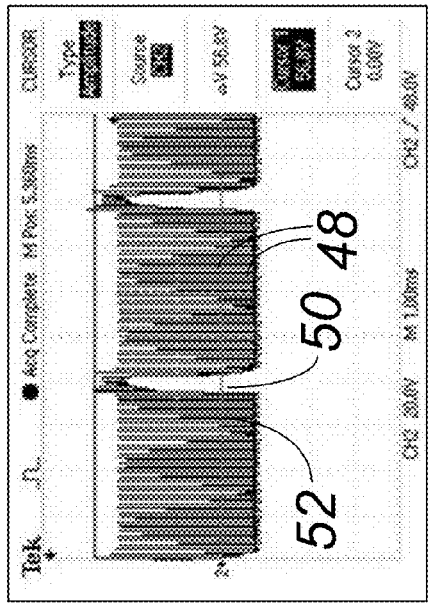
FIG. 12
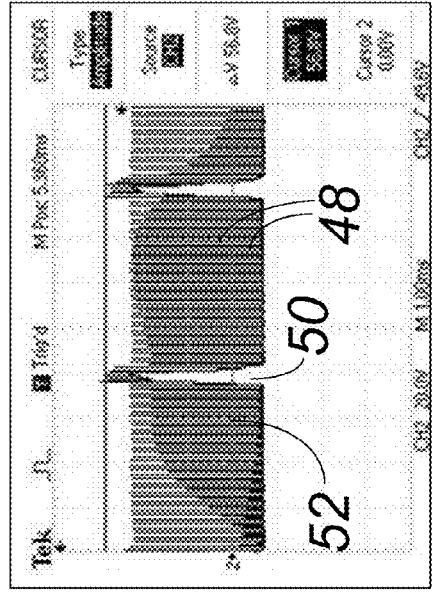
FIG. 13

ELECTRO-THERAPEUTIC STIMULATOR

CROSS-REFERENCE TO RELATED APPLICATION(S)

This application claims priority from Provisional Application No. 61/248,694, filed Oct. 5, 2009, entitled ELECTRO-THERAPEUTIC STIMULATION.

BACKGROUND OF THE INVENTION

The present invention improves upon the apparatus and methods of U.S. Pat. Nos. 5,107,835 and 5,109,848, both of which are incorporated by reference. The ornamental appearance of one version of practicing the present invention is described in U.S. Pat. No. D603,971, incorporated by reference.

It has long been known that the neurological system operates significantly based on electrical impulses. The neurological system works in two directions, both transmitting feeling sensation and pain to the brain, and in firing muscles responsive to impulses from the brain.

It has also long been known that non-biological sources of electrical stimulation can be used to control certain muscles. For instance, the pacemaker works on this principle. Transcutaneous electrical stimulation has also been used in a variety of devices. In most applications, the placement of the electrodes and the electrical signal applied are pre-selected based upon a desired result. The apparatus and methods of U.S. Pat. Nos. 5,107,835 and 5,109,848 operate in this way, using a particular dual periodic-exponential signal form. The periodic-exponential signal form more closely resembles the exponential character of the patient's natural signals. The dual nature of the signal form allows one periodic-exponential signal suitable for sensory stimulation, and a second period-exponential signal suitable for muscle stimulation. In the device of U.S. Pat. Nos. 5,107,835 and 5,109,848, separate rheostat controls enabled a) amplitude control over the muscle stimulation waveform; b) frequency control over primary pulse of the muscle stimulation waveform; and c) control over the "on" portion of the duty cycle of the muscle stimulation waveform. While the device and methods of U.S. Pat. Nos. 5,107,835 and 5,109,848 provided many beneficial results, they did not enable full utilization of the potential for electro-therapeutic stimulation using the dual periodic-exponential signal form. The present invention is directed to an improved electro-therapeutic stimulator for providing enhanced periodic-exponential signal forms.

SUMMARY OF THE INVENTION

The present invention is an electro-therapeutic stimulator and a method of using the electro-therapeutic stimulator. The electro-therapeutic stimulator provides an output signal for application with electrodes to the muscular structure of a patient. The output signal has a first controllable main pulse periodic-exponential signal such as within the range of 1 to 1000 pulses per second, and a second background pulse periodic-exponential signal at a higher frequency such as 1 to 100 kHz. In one aspect, the signal is produced using a class D amplifier and with a transformer optimized for the background pulse rather than for the main pulse. In another aspect, the main pulse is controllable to a high degree of granularity, such has have digital numerical control over frequency, duty cycle and balance. In another aspect, the electro-therapeutic stimulator includes a counter which forces purchasing of durations of signal time for ongoing use of the stimulator. The electro-therapeutic stimulator thus allows greater control over the signal and better muscular and neurological stimulation than previously possible.

BRIEF DESCRIPTION OF THE DRAWINGS

FIGS. 6 and 7 show the background pulse (with no main pulse) using the prior art step up transformer, first with no load and then with a body load.

FIGS. 8 and 9 show the background pulse (with no main pulse) using the preferred step up transformer, first with no load and then with a body load.

FIGS. 10 and 11 show the background pulse and a 245 pps main pulse at peak main pulse voltage using the prior art step up transformer, first with no load and then with a body load.

FIGS. 12 and 13 show the background pulse and a 245 pps main pulse at peak main pulse voltage using the preferred step up transformer, first with no load and then with a body load.

Figure 1:
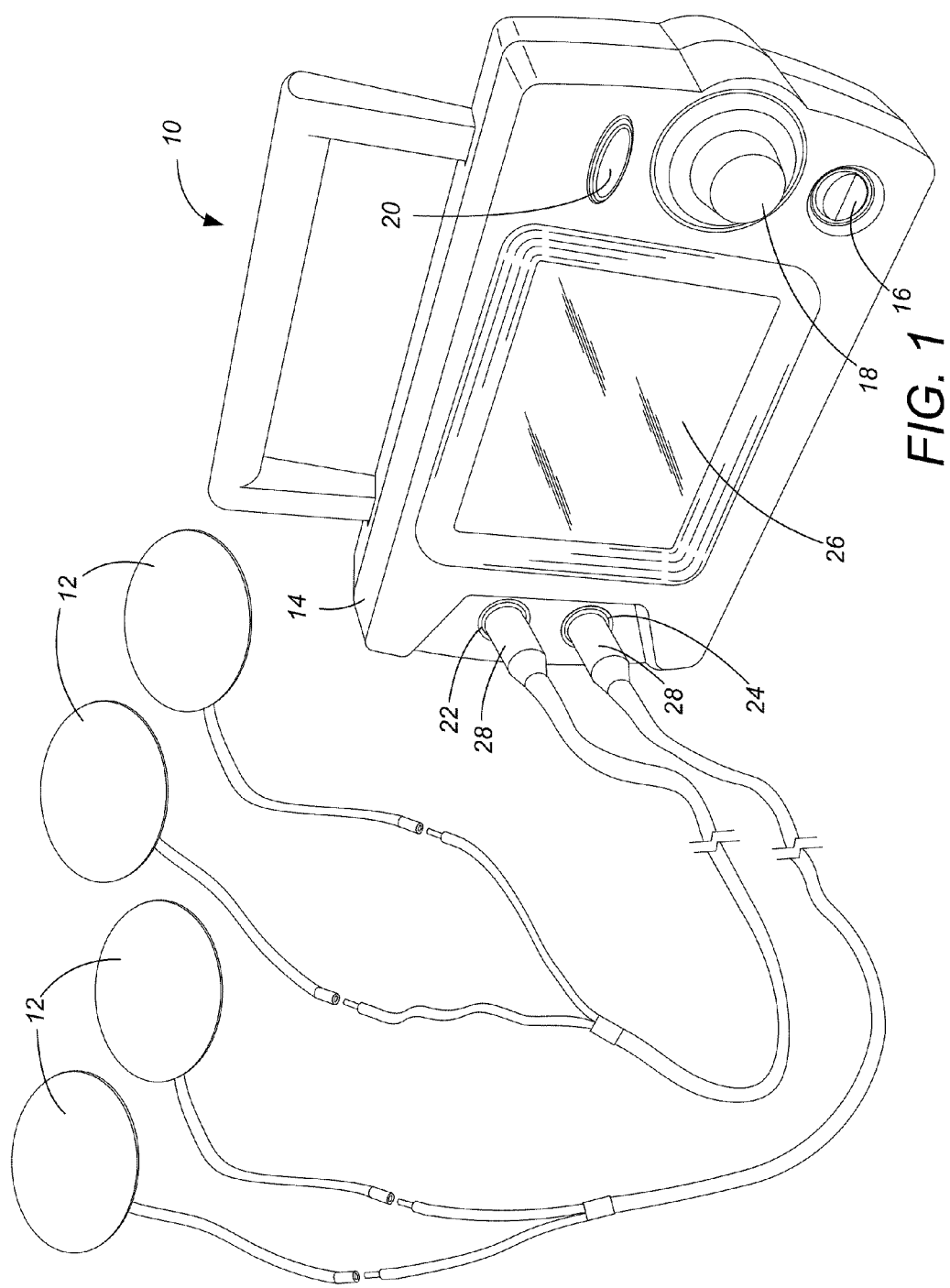
FIG. 1 is a perspective view showing the preferred electro-therapeutic stimulator for use in the present invention.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

The present invention involves methods made possible with an electro-therapeutic stimulator 10 providing tunable, reproducible waveform control of a dual periodic-exponential signal form applied to a patient through electrode pads 12. In the preferred form, the electro-therapeutic stimulator 10 has a housing 14 with an on/off switch 16, an output power dial 18, a power reset switch 20, a left output jack 22, a right output jack 24, and a touch/display screen 26. The electro-therapeutic stimulator 10 may be powered either through a standard electrical power plug 30 (120/240 volts, 50/60 Hz AC input power, shown schematically in FIG. 2), or via a battery 32 (shown schematically in FIG. 2) such as a lithium ion 15 VDC battery. The left and right output jacks 22, 24 each receive a plug 28 for a pair of electrodes 12 (typically one black or negative and the other red or positive) as known in the electro-therapeutic stimulator art. Preferred electrodes 12 are intended to achieve the greatest degree of muscle penetration with the signal, such as electrode pads in excess of one inch in diameter, and more preferably about two inches in diameter, or rectangular pads of around three square inches. The electrode pads 12 can have features based upon their intended use for any given protocol, such as a tacky or pressure-sensitive adhesive layer if the protocol keeps the electrode 12 stationary, or a smoother, less-sticky electrode 12 for protocols requiring moving the electrode 12 across the patient's skin.

Figure 2:
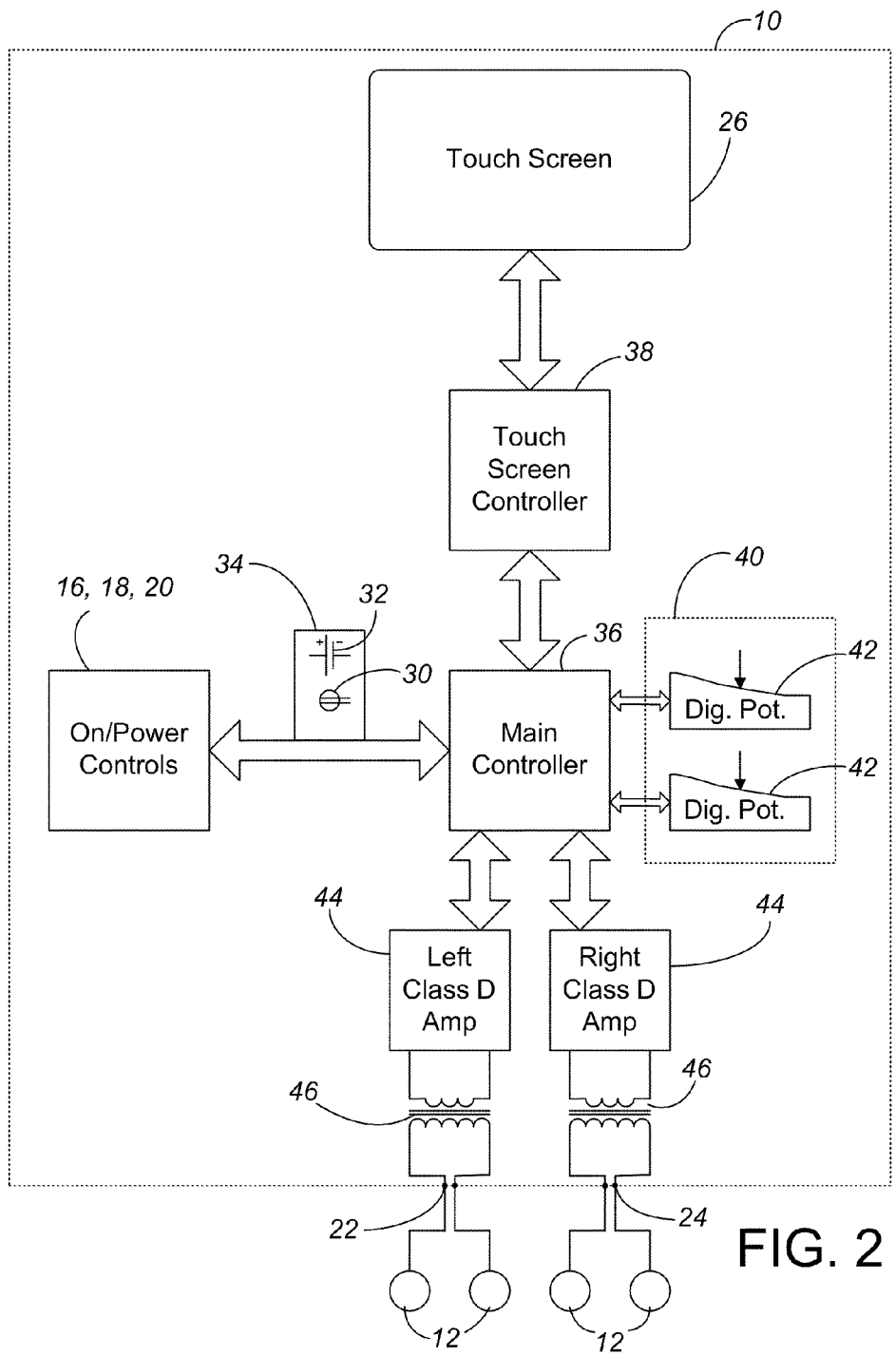
FIG. 2 is a schematic diagram of the primary electric components of the electro-therapeutic stimulator of FIG. 1.

The primary electronic components of the preferred electro-therapeutic stimulator 10 are schematically shown in FIG. 2. The primary input devices are the on and power controls 16, 18, 20 which control the power circuitry 34 for the electro-therapeutic stimulator 10. In the preferred embodiment, the primary component of the power circuitry 34 is a LM3481 Low-Side N-FET high performance controller available from National Semiconductor. The power circuitry 34 provides power as needed for all the components. The primary control for the electro-therapeutic stimulator 10 could be provided in a single integrated circuit chip, but more preferably includes a main controller 36 which is separate from a touch screen controller 38. The preferred main system controller 36 is a PIC18LF6722 enhanced flash microcontroller available from Microchip Technology Inc. of Chandler, Ariz., and a PIC18F2321 microcontroller 38 from Microchip Technology can be used to drive the touch screen 26. The preferred touch screen 26 for the electro-therapeutic stimulator 10 is a 240× 320 pixel four wire resistive touch screen, module no. TSR4855X available from Densitron Corp. of Corona, Calif. The primary function of the main system controller 36 is to generate the signal on the electrodes 12 responsive to the commands input either by the power dial 18 or by the touch screen 26. The wave generator circuit 40, to generate the logarithmic pulse wave profile described generally in U.S. Pat. Nos. 5,107,835 and 5,109,848 but further enhanced as described herein, includes two digital potentiometers 42. In the preferred embodiment, the dual logarithmic pulses are primarily generated in AD5235-025 nonvolatile memory dual 124-position digital potentiometers available from Analog Devices, Inc. of Norwood, Mass. The main right and left channels are driven by the amplifier circuits 44, for which the primary component for each channel is preferably a TPA3001D1 20-W Mono D-class Audio Power Amplifier available from Texas Instruments of Dallas, Tex. The signal from each D-class amplifier 44 is powered for application onto the electrodes 12 by a step up transformer 46.

Figure 3:
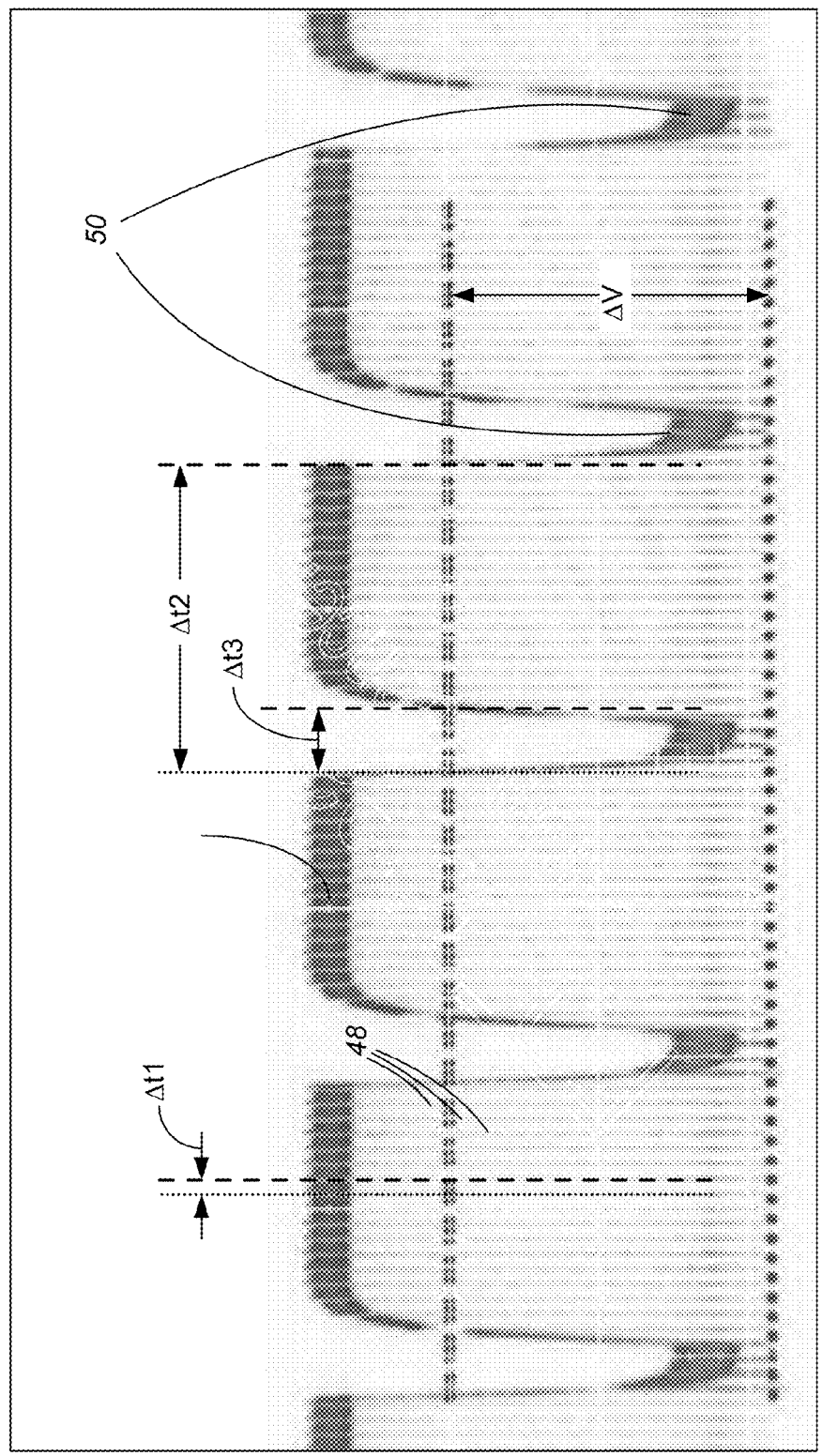
FIG. 3 is an inverted oscilloscope output of a preferred 462 pps, full power signal from the electro-therapeutic stimulator of FIGS. 1 and 2 under no load.
Figure 4:
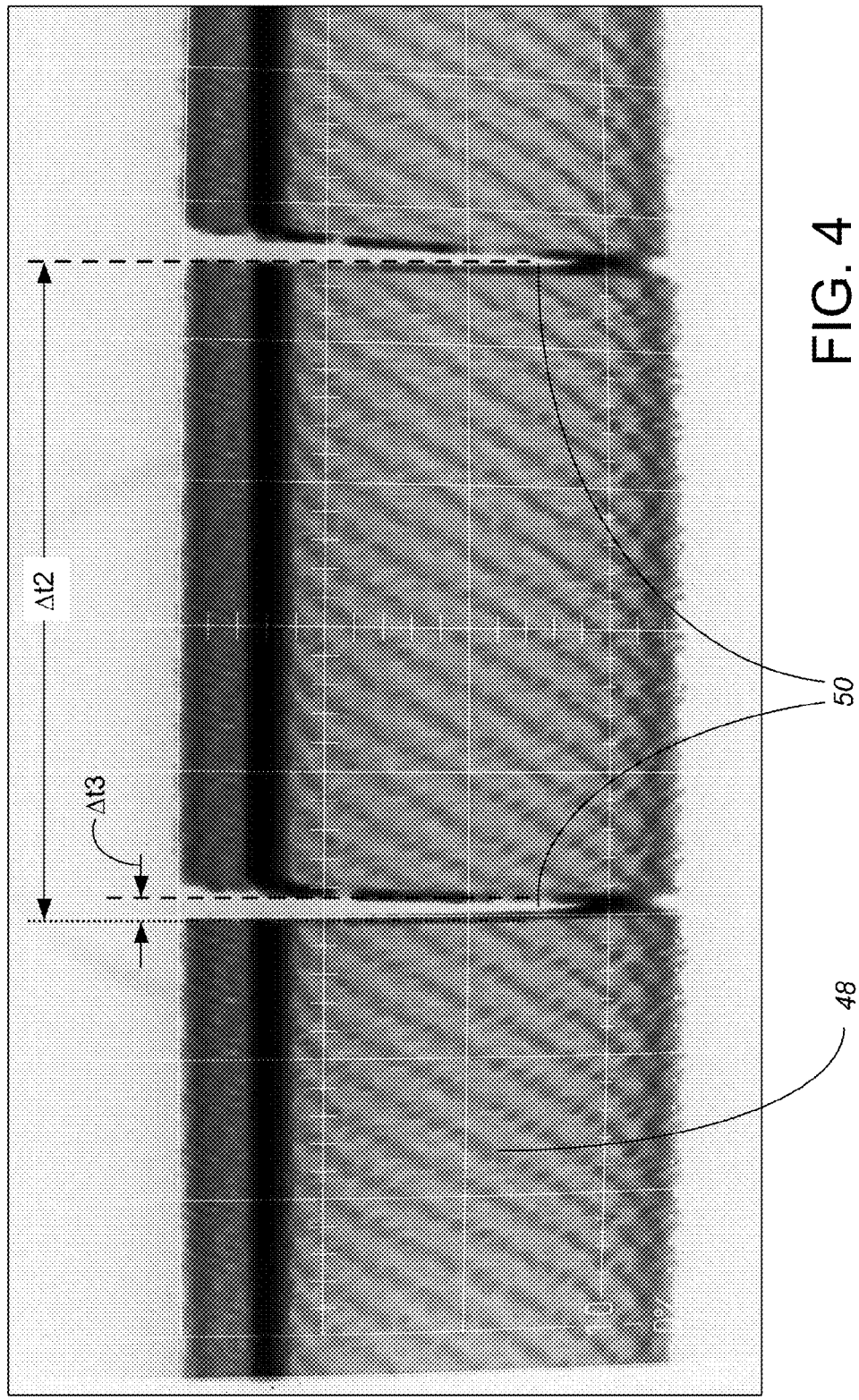
FIG. 4 is an inverted oscilloscope output of a preferred 90 pps, full power signal from the electro-therapeutic stimulator of FIGS. 1 and 2 under no load.

The D-class amplifiers 44 output an electrical waveform having the desired first and second periodic-exponential signal portions, in a pulse width modulated format. Oscilloscope print outs provided by the preferred electro-therapeutic stimulator 10 are shown in FIGS. 3 and 4. A general description of a dual periodic-exponential signal form is provided in U.S. Pat. Nos. 5,107,835 and 5,109,848, but the present invention improves upon this prior art signal in several ways. As best shown in FIGS. 3 and 4, the dual periodic-exponential signal form has a background pulse 48 coupled onto a main pulse 50. The background pulse 48 is at a frequency to stimulate the sensory nerves of the patient, namely, at a frequency over 1 kilohertz and preferably in the range of about 1 to 1000 kilohertz, with the preferred frequency of the background pulse 48 in the range of 8 to 12 kilohertz and the most preferred background pulse 48 at 10 kilohertz. At a background pulse 48 of 10 kHz, each background pulse 48 has a period $\Delta t1$ of 100 µs. The background pulse 48 can be a sine wave, but more preferably has a characteristic RC charge/discharge or "exponential" spike shape. Within this exponential spike shape of the background signal, the preferred background pulse 48 has a power delivery duration of about 25 µs or less, with the background pulse voltage being insignificant over the remaining duration (preferably 75 µs or more) until the next background pulse 48. This background pulse 48 is intended to reproduce a portion of the patient's natural neurological signals. The frequency could be adjusted to match the sensed frequency of a particular individual's natural neurological signals; however, the background pulse frequency of 10 kilohertz has been found effective on a wide variety of people. Thus the preferred electro-therapeutic stimulator 10 is designed with a background pulse frequency of 10 kilohertz and avoids the hardware/firmware expense of designing in controls which could be added to allow the operator to control background pulse frequency.

The main pulse 50 is at a frequency to stimulate the muscles of the patient, namely, in the range of about 1 to 1000 pulses per second, (1 to 1000 hertz or pps), with the preferred frequency of the main pulse 50 being controllable by the operator within the range of 10 to 500 pps, at a preferred control granularity of 1 pulse per second. In the signal shown in FIG. 3, the main pulse 50 is shown as provided at about 482 pps. At a main pulse 50 of 482 pps shown in FIG. 3, each main pulse 50 has a period $\Delta t2$ of just over 2 ms, i.e., about twenty-one background pulses 30 for each main pulse 50. In FIG. 4, the main pulse 50 is shown as provided at about 90 pps. At a main pulse 50 of 90 pps, each main pulse 50 has a period $\Delta t2$ of just over 11 ms, i.e., about 110 background pulses 30 for each main pulse 50. The main pulse 50 also has a characteristic RC charge/discharge or "exponential" spike shape. Within this exponential spike shape of the main pulse signal, the power delivery duration $\Delta t3$ of the main pulse 50 is within the range of 100 to 1000 µs (about 426 µs shown in FIG. 2), with preferred values for main pulse power delivery durations being 460 to 480 µs or alternatively about 320 µs. In general, wider signals (both main pulse 50 and background pulse 48) provide more electrical power to a greater depth of muscle penetration, which can be important for certain protocols.

Figure 5:
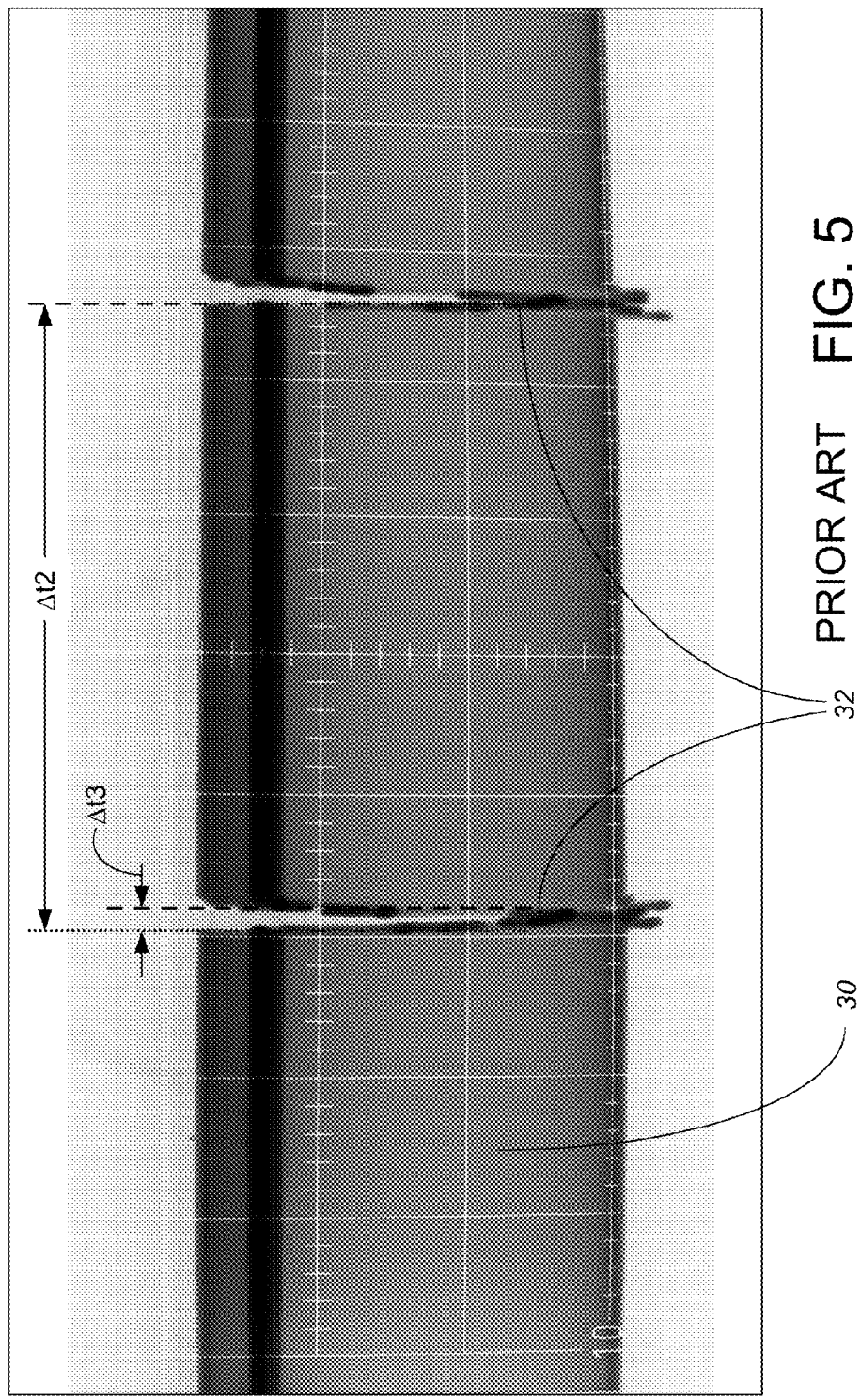
FIG. 5 is an inverted oscilloscope output of a 90 pps, full power signal from the prior art electro-therapeutic stimulator of U.S. Pat. Nos. 5,107,835 and 5,109,848.
Figure 14:
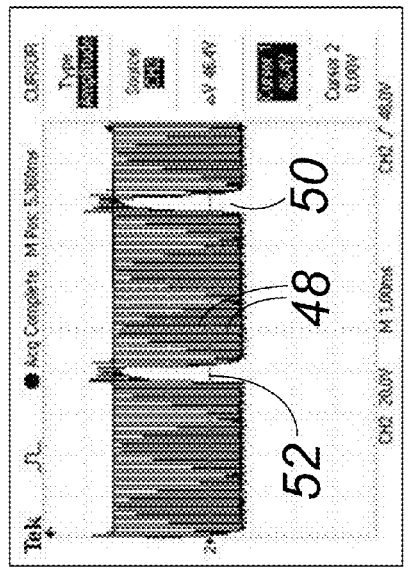
FIGS. 14 and 15 show the background pulse and a 245 pps main pulse at peak background pulse voltage using the prior art step up transformer, first with no load and then with a body load.

When shown at 90 pps (FIG. 4), the harmonics established in the preferred signal by the preferred electro-therapeutic stimulator 10 as visible as the sine wave looking brighter and darker portions of the background signal, which is believed to be due to the D Class amplifier used in signal generation. Contrast these harmonics with the prior art signal shown in FIG. 5, which were obtained with the prior art electro-therapeutic stimulator of U.S. Pat. Nos. 5,107,835 and 5,109,848. It is believed that the pulse width modulation from amplifiers 44 results in the "fuzziness" exhibited in the oscilloscoped output signal of the preferred embodiment as compared to the clearer prior art signal waveform. Pulse width modulated signals are well known in many electronic applications, but Applicant is unaware of any use of a pulse width modulated signal in a therapeutic treatment purpose.

One of the benefits of the pulse width modulated format is that it appears that the high frequency modulation allows the electric waveform to be more palatable and less painful to the tissue being treated. For instance, the preferred configuration of the power amplifiers 44 outputs signals pulse width modulated at about 160 kHz modulation. When this pulse width modulation is applied to a preferred signal, such as the approximately 90 pps Hz signal shown oscilloscoped, the pulse width modulation occurs too fast to appear on the oscilloscope output. Thus, with a pulse width modulated output, the waveform includes three characteristic output frequencies: a main logarithmic pulse of around 482 Hz, a background logarithmic pulse of around 10 kHz, and the pulse width modulation around 160 kHz.

The exact physiological benefit that is provided by the pulse width modulation is not fully understood. However, the pulse width modulation appears to set up additional harmonics (seen in FIG. 4) or other variations of the electric treatment signal being applied so the beneficial aspects of the therapeutic treatment are enhanced or can be performed at a higher, more focused amplitude, while minimizing any deleterious or painful aspects of the therapeutic treatment.

The preferred electro-therapeutic stimulator 10 of the present invention also includes a transformers 46 which differ from the transformers of the prior art stimulator. Namely, the transformers 46 should have a roll off at the background pulse frequency (10 kHz) which is nearly as good as or better than (i.e., almost equal or less than) the roll off of the transformers at the main pulse frequency (10-500 pps).

The present invention involves the concept that the background pulse 48 should be maintained at an amplitude which is on the same order of magnitude as the main pulse 50, and particularly on the same order of magnitude as the main pulse when applied to a full body load. The relative magnitude between the main pulse 50 and the background pulse 48 depends upon the load. The preferred electro-therapeutic stimulator 10, using transformers 46 optimized to provide efficient performance at 10 kHz rather than optimized to provide efficient performance at 10-500 Hz, provides a background pulse which maintains at least 10% of its amplitude when body loaded. The preferred electro-therapeutic stimulator 10, using transformers 46 optimized to provide efficient performance at 10 kHz rather than optimized to provide efficient performance at 10-500 Hz, also has a background signal percentage remaining after body loading which at least half of the percentage remaining after body loading of the main pulse signal. Additionally, when providing a signal having a body loaded main pulse which is at least as large as the body loaded background pulse, the background pulse added on top of the main pulse peak makes up at least 10% of the total signal amplitude.

The 10 kHz frequency is within the audio spectrum heard by humans, but is a rather high tone therein. For instance, while human hearing is generally considered to span the 20-20,000 Hz range, telephone transmissions are often limited beneath about 8 KHz. However, high fidelity music reproduction systems commonly use transformers which maintain signal performance in high audible frequencies. The preferred transformers are iron core step up audio transformers with a 1:21 winding ratio. Good high-frequency response requires careful transformer design and implementing the windings without excessive leakage inductance or stray capacitance. The most preferred transformers are model no. AS-10191 transformers from All Star Magnetics of Vancouver, Wash. The preferred transformers have a package size of about 25 mm (length)×26 mm (width)×20 mm (height) for the electrical package, and about 30 mm (length)×54 mm (width)×31 mm (height) total volume on the circuit board including the sheet metal protector strip ensuring air flow around the electrical package.

The effect of the 10 kHz optimized transformers 46 on the signal under a full body load is further shown with reference to FIGS. 6-17. FIGS. 6 and 7 show the effect of a body load to the 10 kHz background pulse 48 using the prior art transformers which were more optimized for lower frequency ranges. The signals of FIGS. 6 and 7 included no main pulse, and the different widths of the background pulses 48 are merely due to harmonics established in the signal generation (in other words, what matters for this discussion of FIGS. 6-17 is the height (amplitude) of the signal shown on the oscilloscope, not the differing widths of the background pulses 48). As shown in FIG. 6, the no load pulse 48 was oscilloscoped at a total voltage difference of about 215 volts, with more than 80% (178 V) of the voltage being above the 0 V baseline 52. FIG. 7 shows the effect of placing the electrodes 12 for the prior art signal of FIG. 6 across an adult leg, with the y-scale of the output of FIG. 7 at 10 times the y-scale of FIG. 6. The background pulse 48 reduced its voltage to about 20 volts, centered (10 V above, 10 V below) on the 0 V baseline 52. The impedance of the leg tissue thus caused about a 91% reduction of the background signal using the prior art transformers, i.e., only 9% of the no load background signal amplitude was witnessed by the leg tissue.

FIGS. 8 and 9 are using the same signal generation of FIGS. 6 and 7, but with the preferred step up transformers 46 rather than the transformers of the prior art electro-therapeutic stimulator. FIG. 8 shows the no load signal, identical to the no load signal of FIG. 6 (178 V above, 37 V below the 0 V baseline 52 for a total 215 V signal). However, using the identical electrode placement across the human leg (e.g., without moving the electrodes, but merely plugging them into the stimulator), the body load only caused a reduction in the background pulse magnitude to about 53 V, with about 65% (34.4 V) of the voltage above the 0 V baseline 52. (The y-scale of the output of FIG. 9 is at 5 times the y-scale of FIG. 8) Thus, when looking only at a background pulse 48, the transformers of the present invention had a body load reduction of about 75%, i.e., about 25% of the no load background signal amplitude was witnessed by the leg tissue. That is, when considering the voltage passed into the tissue, the transformers 46 which were more optimized for the 10 kHz signal resulted in an increase of 165% more background pulse signal passed into the leg tissue. Even though the prior art transformer may have had good roll off characteristics under no load or under minimal load, under a body load the prior art transformer delivered significantly less background pulse signal. The present invention thus involves the concept that roll off under body loading—particularly for the background pulse 48—may occur significantly in the prior art stimulator and may be improved through transformer selection.

The increased passage of background pulse signal caused by the transformers 46 of the present invention is even more drastic when considering the background pulse 48 with the main pulse 50 as shown in FIGS. 10-17. Like FIGS. 6-9, FIGS. 10-17 show the prior art no-load/body load comparison on top (i.e., FIGS. 10, 11, 14 and 15 are oscilloscope outputs obtained using the prior art transformer) and the no-load/body load of the transformer of the present invention on bottom (i.e., FIGS. 12, 13, 16 and 17 were obtained using the transformers 46 more optimized for 10 kHz performance). In all of FIGS. 10-17, the main pulse 50 was at 245 pps and the background pulse 48 at 10 kHz. FIGS. 10-13 were taken at peak main voltage, while FIGS. 14-17 were obtained with peak background voltage.

As shown in FIGS. 10 and 12, the background pulse 48 in both no-load situations had a total background pulse amplitude between main pulses 50 of about 63 V, with about 74% (47 V) of the voltage above the 0 V baseline 52. The main pulse 50 in both no-load situations had an amplitude of about 59 V, with about 73% (43 V) of the voltage above the 0 V baseline 52. When added on to the peak of the main pulse 50, the background pulse 48 added only about another 14 V in amplitude, i.e., the combined peak background pulse/main pulse signal was a maximum voltage differential of 73 V, made up of about 81% main pulse, 19% background pulse.

Now we look at the effect of adding the body load to the signals of FIGS. 10 and 12. When the body load was added to the signal using the prior art transformer as shown in FIG. 11, the body load affected the background pulse 48 much more than it affected the main pulse 50. The prior art background pulse 48 in the body loaded situation had a total background pulse amplitude between main pulses 50 of only about 5 V. In percentage terms, the body loading caused a reduction of 92% in the amplitude of the background pulse 48 between main pulses 50, such that the percentage remaining after body loading was 8%. With the background pulse 48 reduced so much, the main pulse 48 dominates the background pulse 48 even between main pulses 48, and the amount of the background pulse 48 above and below the 0 V baseline 52 becomes irrelevant. The prior art main pulse 50 in the loaded situation shows an amplitude of about 30 V, with about 87% (26.4V) of the voltage above the 0 V baseline 52, i.e., the body loading caused a reduction of 49% in the amplitude of the main pulse 50 (51% of the main pulse remaining after body loading). When added on to the peak of the main pulse 50, the background pulse 48 became so small that no artifact can be seen in the oscilloscope output, i.e., the body loading caused a 100% reduction of the background pulse signal on the peak of the main pulse 50, such that the combined peak background pulse/main pulse signal was 100% main pulse (0% remaining of the background pulse signal).

When the body load was added to the signal using the transformer of the present invention as shown in FIG. 13, the body load affected the background pulse 48 only slightly more than it affected the main pulse 50. The background pulse 48 from the preferred transformer 46 in the body loaded situation had a total background pulse amplitude between main pulses 50 of about 27 V, i.e., the body loading caused a reduction of 57% in the amplitude of the background pulse 48 between main pulses 50 (43% background pulse remaining after body loading). In other words, the transformer 46 of the present invention resulted in a background pulse percentage magnitude remaining between pulses which was 5.4 times that of the prior art transformer. About 61% of the background pulse 48 between main pulses 50 was above the 0 V baseline 52, meaning that the transformers 46 optimized toward 10 kHz performance still pumped considerable background pulse charge through the leg tissue. The main pulse 50 from the inventive transformer in the loaded situation shows an amplitude of about 44 V, with about 75% (33V) of the voltage above the 0 V baseline 52, i.e., the body loading caused a reduction of 25% in the amplitude of the main pulse 50 (75% main pulse remaining). When added on to the peak of the main pulse 50, the background pulse 48 became about 6 volts, i.e., the combined peak background pulse/main pulse signal was a maximum voltage differential of 50 V, made up of about 88% main pulse, 12% background pulse.

The same type of results are seen when the signal is provided with peak background pulse voltage as shown in FIGS. 14-17. The background pulse 48 in the unloaded situation, using both the prior art (FIG. 14) and inventive (FIG. 16) transformers, had a total background pulse amplitude between main pulses 50 of about 63 V, with about 74% (46.4 V) above the 0 V baseline 52 and 26% (about 17V) below the 0 V baseline 52. The main pulse 50 in both no-load situations had an amplitude of about 60 V, with about 77% (46.4 V) of the voltage above the 0 V baseline 52. When added on to the peak of the main pulse 50, the background pulse 48 added only about another 18 V in amplitude, i.e., the combined peak background pulse/main pulse signal was a maximum voltage differential of 78 V, made up of about 77% main pulse, 24% background pulse.

Figure 15:
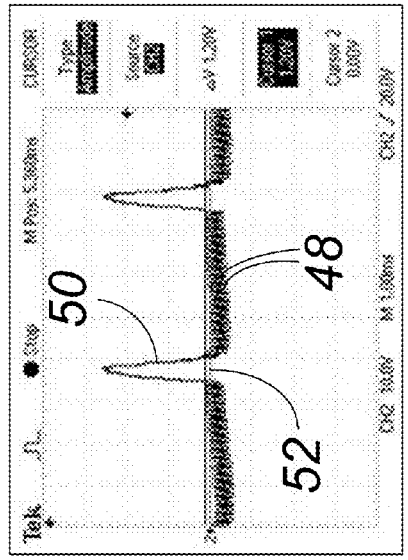
Figure 16:
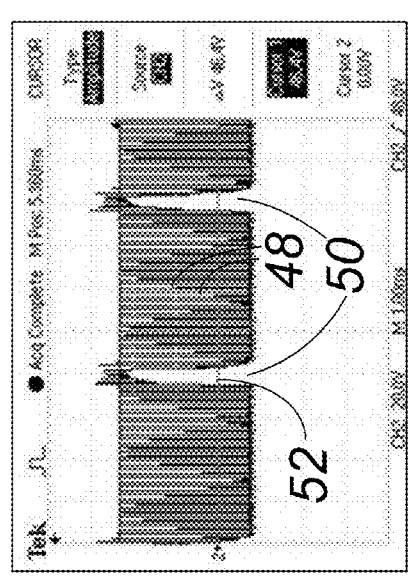
FIGS. 16 and 17 show the background pulse and a 245 pps main pulse at peak background pulse voltage using the preferred step up transformer, first with no load and then with a body load.
Figure 17:
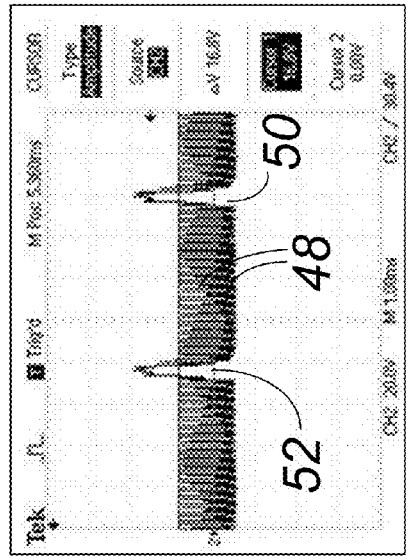
Figure 18:
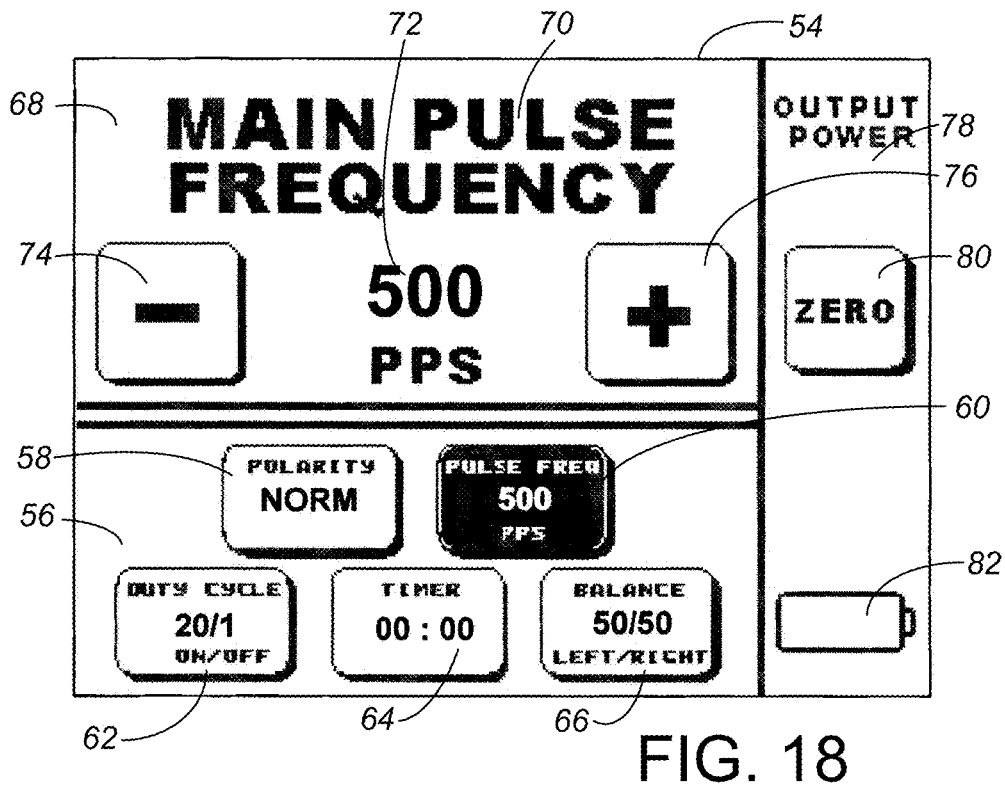
FIG. 18 shows the preferred main pulse frequency screen of the electro-therapeutic stimulator of FIGS. 1 and 2.
Figure 19:
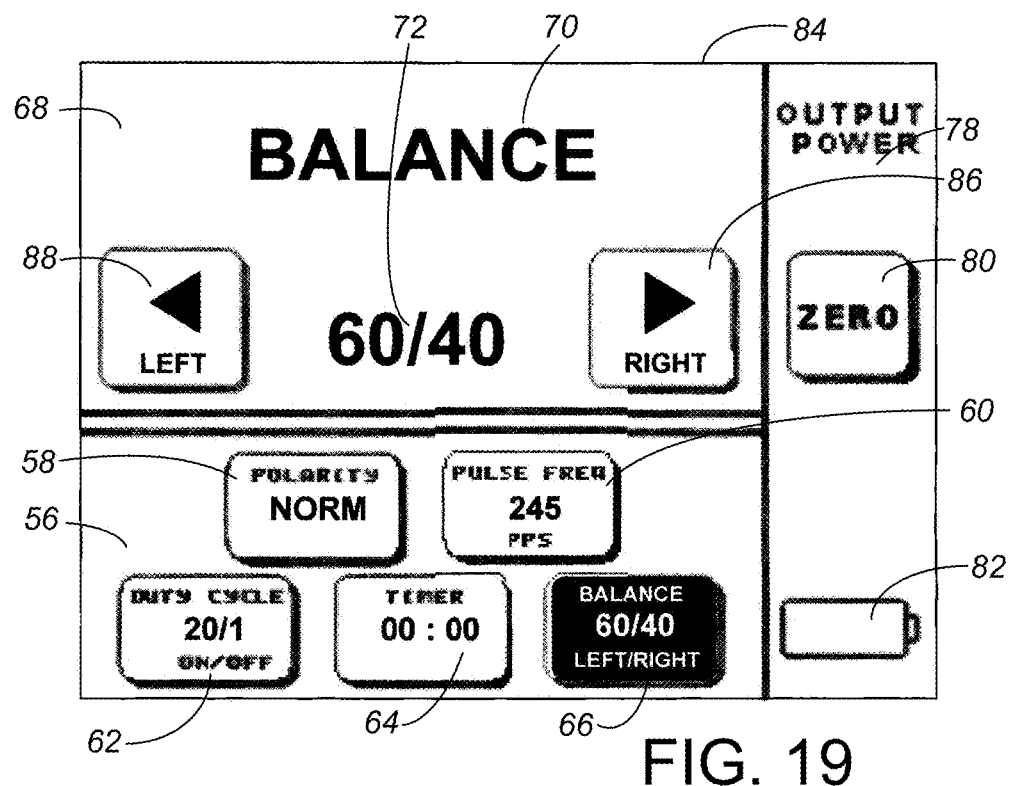
FIG. 19 shows the preferred balance screen of the electro-therapeutic stimulator of FIGS. 1 and 2.
Figure 20:
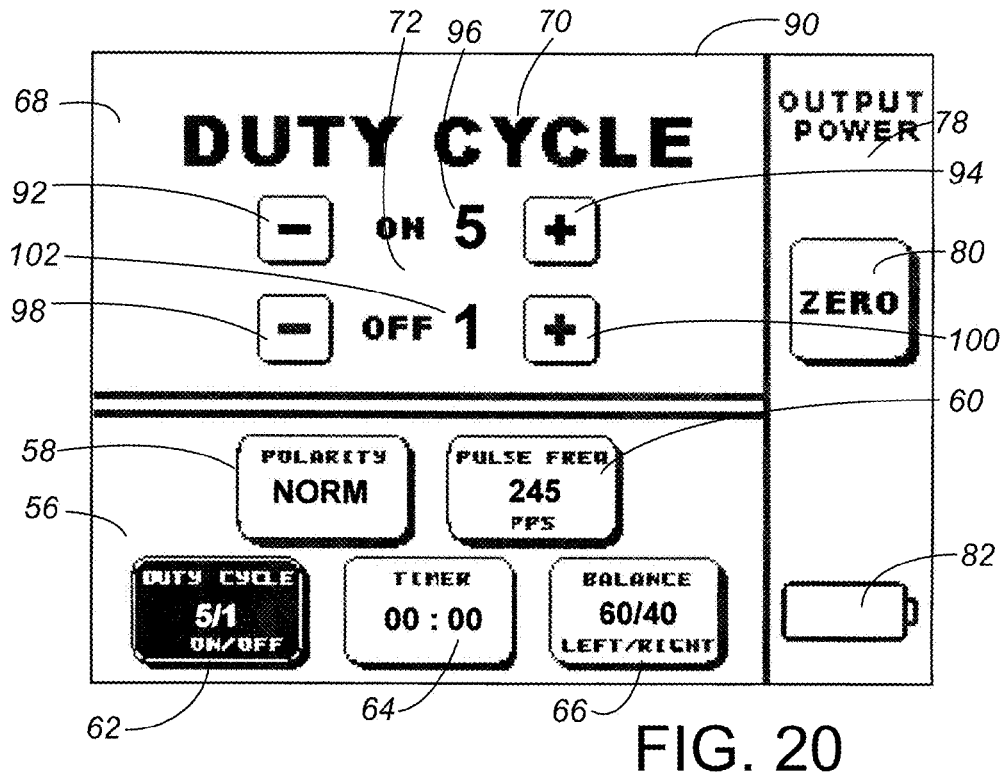
FIG. 20 shows the preferred duty cycle screen of the electro-therapeutic stimulator of FIGS. 1 and 2.

As shown in FIG. 15 (wherein the y-axis scale is doubled relative to the oscilloscope outputs of FIGS. 10-14, 16 and 17, i.e., the output shown in FIG. 15 is at 10V per major division, while all the other outputs are shown at 20V per major division), the prior art background pulse 48 in the body loaded situation had a total background pulse amplitude between main pulses 50 of only about 5 V, i.e., the body loading caused a reduction of 92% in the amplitude of the background pulse 48 between main pulses 50. With the background pulse 48 reduced so much, the main pulse 48 dominates the background pulse 48 even between main pulses 48, and the amount of the background pulse 48 above and below the 0 V baseline 52 is irrelevant. The prior art main pulse 50 in the loaded situation shows an amplitude of about 30 V, with about 88% (27V) of the voltage above the 0 V baseline 52, i.e., the body loading caused a reduction of 48% in the amplitude of the main pulse 50. When added on to the peak of the main pulse 50, the background pulse 48 became so small that no artifact can be seen in the oscilloscope output (even when the y-axis scale was doubled in the displayed output), i.e., the body loading caused a 100% reduction of the background pulse signal on the peak main pulse, such that the combined peak background pulse/main pulse signal was 100% main pulse.

When the body load was added to the signal using the transformer of the present invention as shown in FIG. 16, the body load again affected the background pulse 48 only slightly more than it affected the main pulse 50. The background pulse 48 from the preferred transformer 46 in the body loaded situation had a total background pulse amplitude between main pulses 50 of about 27 V, i.e., the body loading caused a reduction of 57% in the amplitude of the background pulse 48 between main pulses 50. In other words, the transformer 46 of the present invention resulted in a background pulse magnitude between pulses which was increased about 440% relative to the prior art transformer. About 62% of the background pulse 48 between main pulses 50 was above the 0 V baseline 52, meaning that the transformers 46 optimized toward 10 kHz performance again pumped considerable background pulse charge through the leg tissue. The main pulse 50 from the inventive transformer in the loaded situation shows an amplitude of about 42 V, with about 74% (31V) of the voltage above the 0 V baseline 52, i.e., the body loading caused a reduction of 26% in the amplitude of the main pulse 50. When added on to the peak of the main pulse 50, the background pulse 48 became about 7 volts, i.e., the combined peak background pulse/main pulse signal was a maximum voltage differential of 49 V, made up of about 86% main pulse, 14% background pulse.

In more functional terms, even with the transformers 46 being more optimized for the 10 kHz signal, the inherent tendency of step up transformers 46 to act as low pass filters caused the transformer to pump the background pulse 48 less under body loading than it pumped the main pulse 50. But by optimizing the transformers 46 toward the 10 kHz signal, the contribution of the background pulse 48 over the main pulse 50 is still significant even after body loading.

The power level of both the main pulse 50 and the background pulse 48 is operator-variable using the output power dial 18 with at least ten power level increments, and more preferably with eighteen power level increments, and more preferably with at least 100 power level increments, with the most preferred electro-therapeutic stimulator 10 having 1000 power level increments on a scale of 1 to 100. Additional granularity in the power level control adds cost to the design of the electro-therapeutic stimulator 10, and the higher granularity of power control may not be necessary for performing all protocols. When power of the signal is delivered to a patient during an application, the power output of the preferred electro-therapeutic stimulator 10 varies nonlinearly in proportion to the load impedance presented by the body of the patient between the two electrode locations. With the preferred electro-therapeutic stimulator 10, for instance, a patient load resistance of 500 Ohms provides a full power output voltage of 31 Vrms, a patient load resistance of 2 kOhms provides a full power output voltage of 49 Vrms, and a patient load resistance of 10 kOhms provides a full power output voltage of 62 Vrms. The signals shown in FIGS. 3 and 4 are at no load, with the measured ΔV in FIG. 2, to give some indication of scale, of 108V.

The preferred electro-therapeutic stimulator 10 allows reversal of polarity, such that the black electrode pad 12 as normally wired will be negative and the red electrode pad 12 as normally wired will be positive.

Each of the main pulse frequency, the balance and the duty cycle levels are fully and exactly reproducible, to a digital, numeric value, with the touch screen control. From a patient standpoint, this allows a more tunable and reproducible control over the waveform, shown with reference to FIGS. 18 through 21. Specifically, the electro-therapeutic stimulator 10 has enhanced control in a) main pulse frequency; b) balance; and c) duty cycle, as well as having the prior art control over d) power level; and e) polarity.

As to main pulse frequency, the preferred embodiment allows control over the main pulse frequency over a range of 40 to 500 pulses per second, at a control granularity of 1 pulse per second. Control over the frequency of the main pulse 50 is provided via the touch screen 26, with the preferred touch screen display 54 for the main pulse frequency shown in FIG. 18. The main pulse frequency screen 54 includes a lower section 56 with tabs or buttons for a menu driven control. For instance, these buttons include a polarity button 58, a main pulse frequency button 60, a duty cycle button 62, a timer button 64, and a balance button 66. The main pulse frequency screen 54 is displayed when the operator touches the main pulse frequency button 60. The main pulse frequency button 60 toggles to an opposite colored display to indicate that the main pulse frequency settings are currently controllable. The main pulse frequency screen 54 includes an upper section 68 with a title 70 of the screen 54, a value indication 72 of the current setting, and a down button 74 and an up button 76 for changing the main pulse frequency setting. The main pulse frequency screen 54 also includes a right hand section 78 that includes an output power button 80 and a battery indicator 82. A 500 pps value is the default when the electro-therapeutic stimulator 10 is first turned on. The operator can lightly tap the down button 74 or the up button 76 to control the main pulse frequency at 1 pps per tap. Alternatively, the operator may hold (constantly depress) either the down button 74 or the up button 76, resulting in a faster automatic decrementing or incrementing of the main pulse frequency. If none of the buttons 58, 60, 62, 64, 66, 74, 76, 80 are pressed after the operator touches the main pulse frequency button 60, the main pulse frequency screen 54 will stay activated for approximately ten seconds and then will revert to a timer screen. The main pulse frequency button 60 displays the current main pulse frequency setting. The main pulse frequency is accordingly fully and exactly reproducible, to a digital, numeric value, with the touch screen control.

As to balance, the preferred embodiment allows control over the balance over a range of 0/100 to 100/0, at a granularity of 1% increases/decreases to the right and left channels 22, 24. Of course, because the electrodes 12 are mobile and can be placed anywhere on the patient's body, the "right" and "left" labels can be misnomers other than designating two distinct and controllable channels 22, 24. Control over the balance is also provided via the touch screen 26, with the preferred balance screen 84 shown in FIG. 19. The right section is functionally identical to the right section of the main pulse frequency screen 54. The lower section 56 of the balance screen 84 is functionally identical to the lower section 56 of the main pulse frequency screen 54, except that now the balance button 66 is oppositely colored to indicate that the balance settings are currently controllable.

The upper section 68 of the balance screen 84 includes right and left buttons 86, 88 used to adjust the relative power delivered to the electrode pairs. A 50/50 balance value is the default when the electro-therapeutic stimulator 10 is first turned on. The operator can lightly tap the right button 86 or the left button 88 to control the balance at increments of 1% per tap, with a corresponding decrease of the other channel 22, 24. Alternatively, the operator may hold (constantly depress) either the right button 86 or the left button 88, resulting in a faster automatic incrementing and decrementing of the balance between the two channels 22, 24. If none of the buttons 58, 60, 62, 64, 66, 80, 86, 88 are pressed after the operator touches the balance button 66, the balance screen 84 will stay activated for approximately ten seconds and then will revert to the timer screen. The balance button 66 displays the current balance setting. The balance is accordingly fully and exactly reproducible, to a digital, numeric value, with the touch screen control.

As to duty cycle, the preferred embodiment allows control over the duty cycle over an on range of 1 to 20 seconds and over an off range of 0 to 20 seconds, with a granularity over both the on time and the off time during the duty cycle of 1 second. In a more preferred embodiment, the duty cycle can be controlled down to on durations of 0.25 seconds. In the preferred embodiment, this duty cycle control only governs the main pulse 50 (longer period, stronger amplitude) signal. The background signal 48 is not periodically turned off but remains consistent regardless of the duty cycle control. Control over the duty cycle is also provided via the touch screen 26, with the preferred duty cycle screen 90 shown in FIG. 20. The right section 78 is functionally identical to the right section 78 of the main pulse frequency screen 54. The lower section 56 of the duty cycle screen 90 is functionally identical to the lower section 56 of the main pulse frequency screen 54, except that now the duty cycle button 62 is oppositely colored to indicate that the duty cycle settings are currently controllable.

A separate benefit of the preferred signal generation is the ramping between the "on" and "off" modes of the primary duty cycle. The ramping smoothes between the fully on and fully off voltage, such as a ramping occurring during about 2 seconds of the duty cycle. Similar to the pulse width modulation, the ramping allows the electric waveform to be more palatable and less painful to the tissue being treated. In the preferred embodiment, the main ramping is implemented in firmware.

In one preferred embodiment, with an "off" cycle of 6 seconds or more, there is a three second ramp up to the full power for the "on" duration, and a three second ramp down to zero main pulse power during the "off" duration of the duty cycle. In a different preferred embodiment, there is no associated ramp up and ramp down of the power with any "off" duration, with the main pulse 50 delivered as an overall square wave (for instance, at 90 pps and an "on" duration of 1 second, 90 full power main pulses 50 will be delivered during the on duration, with no partial power main pulses 50 either immediately before or after the "on" cycle). In a different preferred embodiment of electro-therapeutic stimulator 10, the duty cycle allows a faster full power main pulse 50 without a ramp, such as providing the main pulse 50 at a ¼ second on and 1 second off. In another preferred embodiment, longer duty cycles include a ramp, but the short duty cycles (less than 6 seconds) include no ramp.

The upper section 68 of the duty cycle screen 90 includes the title 70 of the screen. Below the title 70, the duty cycle screen 90 has a minus button 92 and a plus button 94 for the on cycle, with a value 96 indicating the current on duration. Below that, the duty cycle screen 90 has a minus button 98 and a plus button 100 for the off cycle, with a value 102 indicating the current off duration. A 1 second on, 0 second off (i.e., continuous) duty cycle setting is the default when the electro-therapeutic stimulator 10 is first turned on. The operator can lightly tap any of the four buttons 92, 94, 98, 100 to control the duty cycle at either 1 second or ¼ second per tap. Alternatively, the operator may hold (constantly depress) any the four buttons 92, 94, 98, 100, resulting in a faster automatic decrementing or incrementing of the on or off durations of the duty cycle. If none of the buttons 58, 60, 62, 64, 66, 80, 92, 94, 98, 100 are pressed after the operator touches the duty cycle button 62, the duty cycle screen 90 will stay activated for approximately ten seconds and then will revert to the timer screen. The duty cycle button 62 displays the duty cycle setting. The duty cycle is accordingly fully and exactly reproducible, to a digital, numeric value, with the touch screen control.

The enhanced tunability and reproducibility of the main pulse frequency, balance and duty cycle permits surprisingly beneficial results in terms of application to a specific condition being suffered by a specific patient. During application of the waveform to the patient, feedback is taken from the patient which is used to gauge the effectiveness of the waveform. Through this feedback, the waveform is tuned to better treat the patient's condition. Preferred feedback mechanisms include monitoring the patient's heart rate, monitoring the patient's respiratory rate; visual inspection of muscle firings on the patient's body, and pain or physical sensation feedback given (typically verbally) from the patient.

For instance, the electrodes may be applied for enhanced healing of the patient's left quadricep. Possibly due to a learned walking motion, most patients' left quadricep is coupled to the patient's right bicep. At one particular frequency of the main pulse frequency (for instance, at 128 pps), possibly restricted to a specific duty cycle, power level, balance and polarity (for instance, at a 3 on/2 off, power level 8, 50/50 balanced, normal polarity waveform), application of the waveform to the left quadriceps will cause the patient's right bicep to responsively fire. The firing of the right bicep can be visually identified while the technician is tuning the waveform, and further can be felt and identified by the patient while undergoing treatment.

For many desired treatments, the applied waveform can produce surprisingly different therapeutic results based on whether the main pulse frequency is properly tuned (at 128 pps) or improperly tuned (for instance, at 130 pps). Applicant theorizes that the importance of the proper tuning of the waveform is based upon different electrical energy absorption rates of different tissue structures (scar tissue versus healthy tissue, for instance), possibly at a harmonic that exactly matches the electrical transmission rate and size of that patient's physical layout of scar and healthy tissue. The most beneficial application of the electronic waveform thus requires precise tuning of the waveform. That is, applying the waveform at 130 pps for one particular patient may accelerate healing only slightly, while applying the waveform at 128 pps for that patient may accelerate healing significantly.

For multiple treatments, it can be very important that treatment again be provided at 128 pps. That is, not only does the fine granularity of the controls of the preferred embodiment allow proper tuning, but then the waveform can be quickly and easily reproduced at exactly 128 pps. While the prior electrical stimulator provided dial inputs of main pulse frequency, output power, balance and duty cycle, those dial controls were not nearly as exact as the present invention, and provided no confidence in reproducibility of the type required for the most beneficial tuning and use of the present invention.

Control over the duty cycle is important for tuning of the waveform to the particular patient and desired treatment modality as described above. Control over the duty cycle is also important and appropriate for use of the present invention beyond stationary patients. That is, the present invention can be used to stimulate muscles, muscle groups, joints, tendons, ligaments, bones or other tissue coupled with an exercise, training or weight bearing regimen on those body structures. As one example, the present invention can be applied on a patient's leg during rehabilitation of a knee joint. While the electronic signal provides benefits even when applied to a stationary knee joint, additional benefits can be obtained by exercising the knee joint during application of the signal. The patient may be instructed to perform a series of deep knee bends while the electrical signal is being applied to the knee. The patient may be comfortable performing a down motion of a deep knee bend for a two second duration, remaining in the down position for one second, rising/extending out of the deep knee bend for a three second duration, and resting for two seconds before performing the next deep knee bend. Depending upon the particular tissue being treated, the electrical signal may be focused for application during only the rising/extending motion. In such circumstances, a duty cycle of three seconds on and six seconds off can be used. With such a duty cycle, the patient can time the deep knee bends so the primary signal is on during the rising/extending motion, off during the remainder of the deep knee bend exercise regimen. The ability to match timing of the duty cycle with a comfortable exercise regimen provides more focused healing and strengthening benefits of the therapy. Depending upon the desired results, the present invention allows the flexibility to time the on portion of the duty cycle at any portion of the exercise being performed.

An additional beneficial aspect of the present invention results from multiple, simultaneous targeted treatments. In particular, one stimulator can be used to provide a particular, tuned waveform to electrodes placed at one location of the body, while a second stimulator can be used at a different tuned waveform to electrodes placed at a different location of the body.

Figure 21:
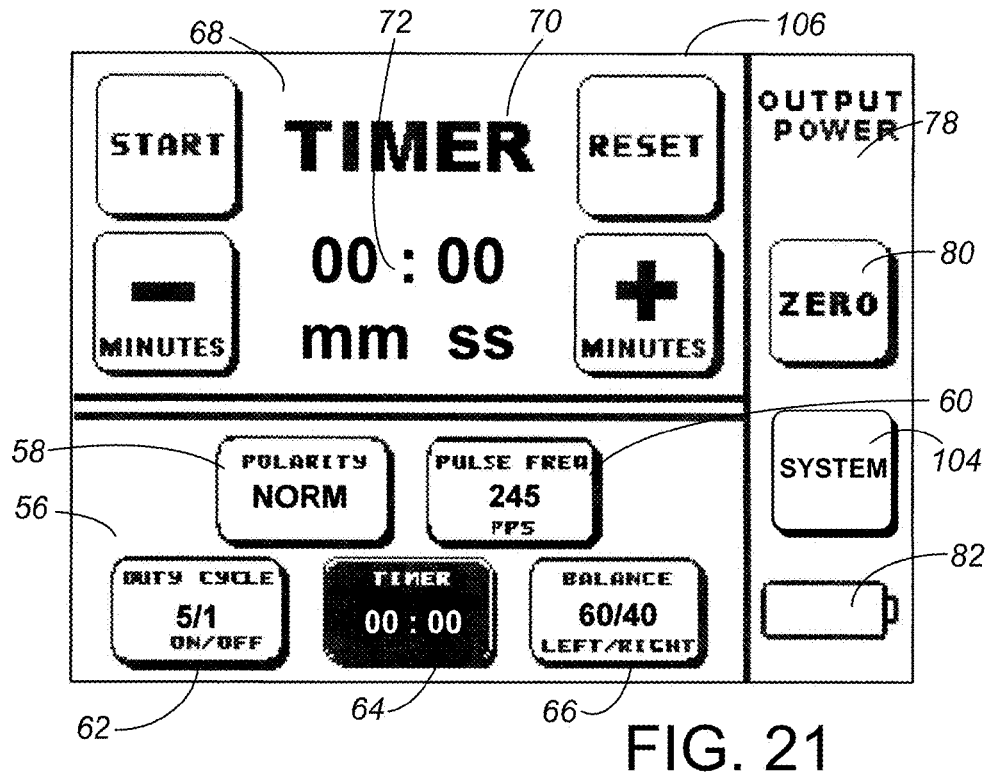
FIG. 21 shows the preferred system screen of the electro-therapeutic stimulator of FIGS. 1 and 2.
Figure 22:
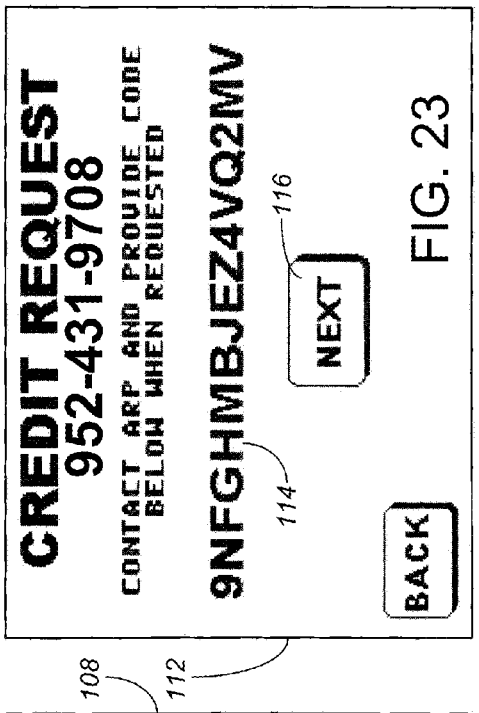
FIGS. 22-25 show the preferred payment processing screens of the electro-therapeutic stimulator of FIGS. 1 and 2.

The preferred electro-therapeutic stimulator 10 includes countdown timer and a shut-off mechanism for discontinuing the electric treatment signal waveform on the output 22, 24 when the counter reaches a selected termination value. The payment for treatment screens of the preferred electro-therapeutic stimulator 10 are explained with reference to FIGS. 21-25. A system button 104 is shown in FIG. 21, and appears when the electro-therapeutic stimulator 10 is first turned on as part of the default screen 106. The preferred electro-therapeutic stimulator 10 only provides power so long as the user has purchased sufficient time on the machine 10. When the user taps the system button 104, the credit screen 108 shown in FIG. 22 will appear showing how much time of use is left in hours and minutes. The credit screen 108 needs to be activated when the electro-therapeutic stimulator 10 quits supplying power because the hours and minutes previously purchased are at zero. The electro-therapeutic stimulator 10 can accordingly be released to a patient for the patient to perform electro-therapeutic stimulation at home and in accordance with his or her own schedule rather than at a prescribing operator's (such as a licensed physician's) office. When the user needs to purchase more time, the user presses the credit request button 110 on the credit screen 108.

Figure 23:
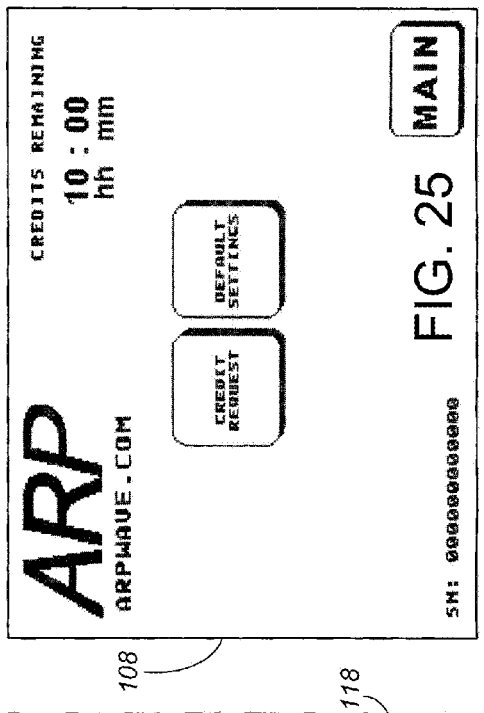
Figure 24:
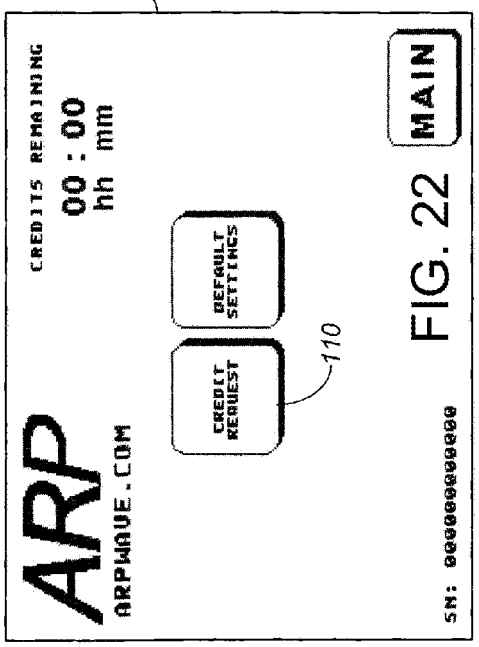
Figure 25:
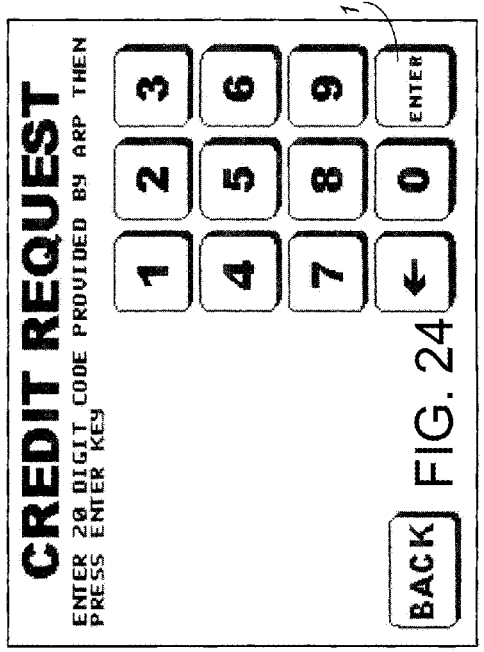

Responsive to pressing the credit request button 110, the electro-therapeutic stimulator provides a challenge code screen 112 shown in FIG. 23. The challenge code screen 112 preferably provides a challenge code 114, with the preferred challenge code 114 including several different types of information. In the preferred embodiment, the 16 character code includes: a 12 character device serial number/code, a three character rolling request code, and a one character check/validity code. Each of these codes are preferably rearranged/reordered, e.g., the character representing a first digit of the serial number/code might be the eighth character of the challenge code 114, etc. Each character is also preferably encrypted, e.g., a character "J" of the challenge code 114 may represent a digit 8 of the serial number/code. Additionally, the challenge code 114 may further include one or more random characters. Further, either the rearrangement/reordering or the encryption key or both may cycle through a series of encodings, e.g., which encryption key and which reordering key is used may depend upon the rolling request code. The device thus provides a challenge code 114 which is decipherable at the "time-issuing location" (in this embodiment, at a computer accessible at the 952-431-9708 phone number) to both provide the serial number of the device issuing the challenge code 114 and verify that the challenge code 114 is authentically issued by that serial number device, without allowing the user to understand or separately devise a verifiable challenge code 114.

When a verifiable challenge code 114 is presented by the user, software at the time-issuing location computes a response code which is provided to the user. The response code includes both an algorithm-generated response challenge code and several additional characters which tell the device how much additional time credits have been purchased. In the preferred embodiment, the 20 digit response code includes: a 12 digit device serial number/code, a 2 digit time added code, 2 digits of response hash codes, and a 4 digit rolling challenge response code. Again, each of these codes can be rearranged/reordered and encrypted, and the response challenge code might further include one or more random characters. The user presses the next button 116 on the challenge code screen 112, which displays a response code screen 116 shown in FIG. 24. The user then inputs the response code which has been provided, and presses the enter button 118.

The firmware on the device 10 deciphers the response challenge code to a) verify that the response challenge code is for the serial numbered device; b) verify that the rolling challenge response code matches the rolling request code; and c) identify how much additional time was provided. Upon verifying that the 20 digit response challenge code is a valid response code for that device 10 and that time request, the device 10 permits additional signal time, shown in the credit screen 108 of FIG. 25. In this example, the user has purchased another 10 hours of usage time. In another example, the user could purchase time for unlimited use of the electro-therapeutic stimulator 10. The electro-therapeutic stimulator 10 can then be used to provide a signal across the electrodes 12 for another 10 hours.

As another example, the authentication challenge code method taught by U.S. Pat. No. 5,841,866 can be used, even though the codes are not wirelessly transmitted and received but rather are voice delivered by the user of the device. U.S. Pat. No. 5,841,866 is incorporated by reference.

Although the present invention has been described with reference to preferred embodiments, workers skilled in the art will recognize that changes may be made in form and detail without departing from the spirit and scope of the invention.

The invention claimed is:

1. A method of electro-therapeutic stimulation, comprising:
   tuning an electric treatment signal to a desired treatment modality, wherein the electric treatment signal waveform comprises:
      a first periodic-exponential signal having a first main pulse frequency and duty cycle;
   wherein the tuning comprises adjusting one or more of the following waveform parameters:
      main pulse frequency, at an adjustment granularity of less than 25 pulses per second; and
      duty cycle, at an adjustment granularity of less than 5 seconds; and
   performing a first treatment using the tuned electric treatment signal waveform by applying the waveform to electrodes placed on the patient's body.

2. The method of claim 1, further comprising:
   after a rest duration, performing a second treatment using the identical tuned electric treatment signal waveform.

3. The method of claim 1, wherein the electric treatment signal waveform is applied to the patient using two sets of electrodes, and wherein the tuning comprises adjusting balance of signal intensity between the two sets of electrodes, at an adjustment granularity of less than 10%.

4. The method of claim 1, wherein the tuning comprises:
   applying the untuned waveform to electrodes placed on the patient's body;
   taking feedback from the patient about the effect of the untuned waveform, the feedback comprising one or more of the following:
      monitoring heartrate;
      monitoring respiratory rate;
      monitoring muscle firing; and
      monitoring patient pain levels; and
   adjusting the waveform based upon the feedback.

5. The method of electro-therapeutic stimulation of claim 1, wherein the first periodic-exponential signal has a first period; and wherein the electric treatment signal waveform further comprises:
   a second periodic-exponential signal having a second period overlaid on the first periodic-exponential signal, the second period being different than the first period;
   and wherein the method further comprises:
   applying a second electric treatment signal waveform to electrodes positioned at second locations on a patient's body, wherein the second electric treatment signal waveform comprises:
      a third periodic-exponential signal having a third period; and
      a fourth periodic-exponential signal having a fourth period overlaid on the third periodic-exponential signal, the fourth period being different than the third period, the fourth period also being different than the second period.

6. The method of electro-therapeutic stimulation of claim 1,
wherein at least a portion of the electric treatment signal has a duty cycle; and wherein the method further comprises:
performing an exercise for the tissue being treated during application of the electric treatment signal, the exercise being performed at a rate that corresponds with the duty cycle of the electric treatment signal.

7. A tunable electro-therapeutic stimulation device comprising:
a signal generation circuit for generating an electric treatment signal waveform, wherein the electric treatment signal waveform comprises:
a first periodic-exponential signal having a first main pulse frequency and a duty cycle;
wherein the device permits tuning including adjusting one or more of the following waveform parameters:
main pulse frequency, at an adjustment granularity of less than 25 pulses per second; and
duty cycle, at an adjustment granularity of less than 5 seconds.

8. The tunable electro-therapeutic stimulation device of claim 7, wherein the first periodic-exponential signal has a first period in the range of 1 to 1000 pulses per second; and wherein the electric treatment signal waveform further comprises:
a second periodic-exponential signal having a second period overlaid on the first periodic-exponential signal, the second period in the range of 1 to 100 kHz;
the device further comprising a step up transformer increasing the voltage of the electric treatment signal waveform for application to an output, the step up transformer being optimized for the frequency of the second periodic-exponential signal.

9. The tunable electro-therapeutic stimulation device of claim 8, wherein the step up transformer maintains at least 10% of the amplitude of the second periodic-exponential signal when the output is body loaded, as compared to an unloaded output.

10. The tunable electro-therapeutic stimulation device of claim 8, wherein, when providing a signal having a body loaded main pulse which is at least as large as the body loaded background pulse, the background pulse added on top of the main pulse peak makes up at least 10% of the total signal amplitude.

11. The tunable device of claim 7, wherein the device comprises a display providing a digital, numeric value for one or more of the following waveform parameters:
main pulse frequency or period;
duty cycle; and
balance.

12. The tunable electro-therapeutic stimulation device of claim 7 wherein the first periodic-exponential signal has a first period; and wherein the electric treatment signal waveform further comprises:
a second periodic-exponential signal having a second period overlaid on the first periodic-exponential signal, the second period being different than the first period;
the device further comprising:
a duty cycle control for changing the duty cycle of the signal generation circuit, wherein the duty cycle control can independently adjust the duration that at least the first periodic-exponential signal is on during each duty cycle and the duration at least the first periodic-exponential signal is off during each duty cycle.

13. The tunable electro-therapeutic stimulation device of claim 12, wherein the duty cycle control allows selection of the number of seconds that the first periodic-exponential signal is on during each duty cycle.

14. The tunable electro-therapeutic stimulation device of claim 13, wherein the duty cycle control allows selection of the number of seconds that the first periodic-exponential signal is off during each duty cycle.

15. The tunable electro-therapeutic stimulation device of claim 14, wherein the duty cycle control allows selection of the number of seconds that the first periodic-exponential signal is on during each duty cycle to a value from 1 to 20 seconds, and wherein the duty cycle control allows selection of the number of seconds that the first periodic-exponential signal is off during each duty cycle to a value from 0 to 20 seconds.

16. The tunable electro-therapeutic stimulation device of claim 7, further comprising:
at least one output for providing the electric treatment signal waveform to electrodes for application on a patient's body part to be stimulated;
a counter for assessing the duration that the electric treatment signal waveform is applied to the output;
a shut-off mechanism for discontinuing the electric treatment signal waveform on the output when the counter reaches a selected termination value; and
a change device for adjusting the counter value and/or termination value upon making payment.

17. The tunable electro-therapeutic stimulation device of claim 16, wherein the counter is a timer for timing the duration that the electric treatment signal waveform is applied to the output.

* * * * *